United States Patent
Qiao et al.

(10) Patent No.: US 12,269,786 B2
(45) Date of Patent: Apr. 8, 2025

(54) PREPARATION METHOD AND PRODUCTION DEVICE FOR PROPYLENE

(71) Applicants: CHINA PETROLEUM & CHEMICAL CORPORATION, Beijing (CN); SINOPEC DALIAN RESEARCH INSTITUTE OF PETROLEUM AND PETROCHEMICALS CO., LTD., Liaoning (CN)

(72) Inventors: Kai Qiao, Liaoning (CN); Feng Zhou, Liaoning (CN); Xiuna Yang, Liaoning (CN); Huixia Ma, Liaoning (CN); Rui Jiang, Liaoning (CN); Shumei Zhang, Liaoning (CN); Ping Jin, Liaoning (CN); Shaozhong Peng, Liaoning (CN)

(73) Assignees: CHINA PETROLEUM & CHEMICAL CORPORATION, Beijing (CN); SINOPEC DALIAN RESEARCH INSTITUTE OF PETROLEUM AND PETROCHEMICALS CO., LTD., Liaoning (CN)

( * ) Notice: Subject to any disclaimer, the term of this patent is extended or adjusted under 35 U.S.C. 154(b) by 0 days.

(21) Appl. No.: 18/245,982

(22) PCT Filed: Oct. 29, 2021

(86) PCT No.: PCT/CN2021/127293
§ 371 (c)(1),
(2) Date: Mar. 20, 2023

(87) PCT Pub. No.: WO2022/089570
PCT Pub. Date: May 5, 2022

(65) Prior Publication Data
US 2023/0357102 A1    Nov. 9, 2023

(30) Foreign Application Priority Data

Oct. 31, 2020  (CN) .......................... 202011196836.5
Oct. 31, 2020  (CN) .......................... 202011196837.X
(Continued)

(51) Int. Cl.
C07C 1/24      (2006.01)
C07C 1/207     (2006.01)
C07C 7/04      (2006.01)

(52) U.S. Cl.
CPC .............. *C07C 1/24* (2013.01); *C07C 1/2076* (2013.01); *C07C 7/04* (2013.01); *C07C 2521/04* (2013.01); *C07C 2521/06* (2013.01)

(58) Field of Classification Search
CPC .... C07C 1/24; C07C 1/20; C07C 7/04; C07C 1/2076; Y02P 20/52
See application file for complete search history.

(56) References Cited

U.S. PATENT DOCUMENTS 5,475,183 A * 12/1995 Araki .................. C07C 1/24
                                               585/638
2009/0259086 A1  10/2009 Bailey et al.
(Continued)

FOREIGN PATENT DOCUMENTS

CN    1043694 A      7/1990
CN    101001822 A    7/2007
(Continued)

OTHER PUBLICATIONS

Ma, Hui-Xia et al.; "Thermodynamic analysis on dehydration reaction of isopropanol to produce propylene"; Modern Chemical Industry; vol. 40, No. 6; Jun. 2020; pp. 196-203.
(Continued)

*Primary Examiner* — Sharon Pregler
(74) *Attorney, Agent, or Firm* — NKL Law; Allen Xue

(57) ABSTRACT

A process for producing propylene involves dehydration of isopropanol. The dehydration process includes a step of
(Continued)

subjecting a starting material containing isopropanol to a dehydration reaction in the presence of a dehydration catalyst comprising alumina to produce a product containing propylene. The starting material has a water content of 0.1 to 10.0 wt % (relative to 100 wt % of the total mass of the starting material), and the product has a total content of C2 unsaturated impurities and C3-C4 unsaturated impurities of 80 ppm or less (relative to 100 wt % of the total mass of the product).

22 Claims, 1 Drawing Sheet

(30) Foreign Application Priority Data

Oct. 31, 2020 (CN) .......................... 202011198803.4
Oct. 27, 2021 (CN) .......................... 202111253863.6

(56) References Cited

U.S. PATENT DOCUMENTS

| | | |
|---|---|---|
| 2012/0010453 A1 | 1/2012 | Ohkubo et al. |
| 2014/0179972 A1 | 6/2014 | Taheri et al. |
| 2016/0122257 A1 | 5/2016 | Ishibashi |

FOREIGN PATENT DOCUMENTS

| | | | |
|---|---|---|---|
| CN | 101336217 | A | 12/2008 |
| CN | 101863731 | A | 10/2010 |
| CN | 102690172 | A | 9/2012 |
| CN | 102728361 | A | 10/2012 |
| CN | 103370420 | A | 10/2013 |
| CN | 103449967 | A | 12/2013 |
| CN | 103508833 | A * | 1/2014 |
| CN | 103508833 | B | 2/2015 |
| CN | 103772145 | B | 9/2016 |
| EP | 2740718 | A1 | 6/2014 |
| JP | H02174737 | A | 7/1990 |
| JP | H03133937 | A | 6/1991 |
| WO | 2009043574 | A1 | 4/2009 |
| WO | 2010106966 | A1 | 9/2010 |
| WO | 2014196517 | A1 | 12/2014 |
| WO | 2015135641 | A1 | 9/2015 |

OTHER PUBLICATIONS

Liu, Chunyan et al.; "Dehydration of Isopropanol to Propylene Catalyzed by Acid Catalysts"; Industrial Catalysis; vol. 19, No. 5; May 2011; pp. 40-44.

Lopez, T et al.; "Catalytic properties of silico-aluminates prepared by the sol-gel method: isopropanol dehydration"; Journal of Non-Crystalline Solids; vol. 147-148, ISSN: 0022-3093; Jan. 1, 1992; pp. 769-772.

* cited by examiner

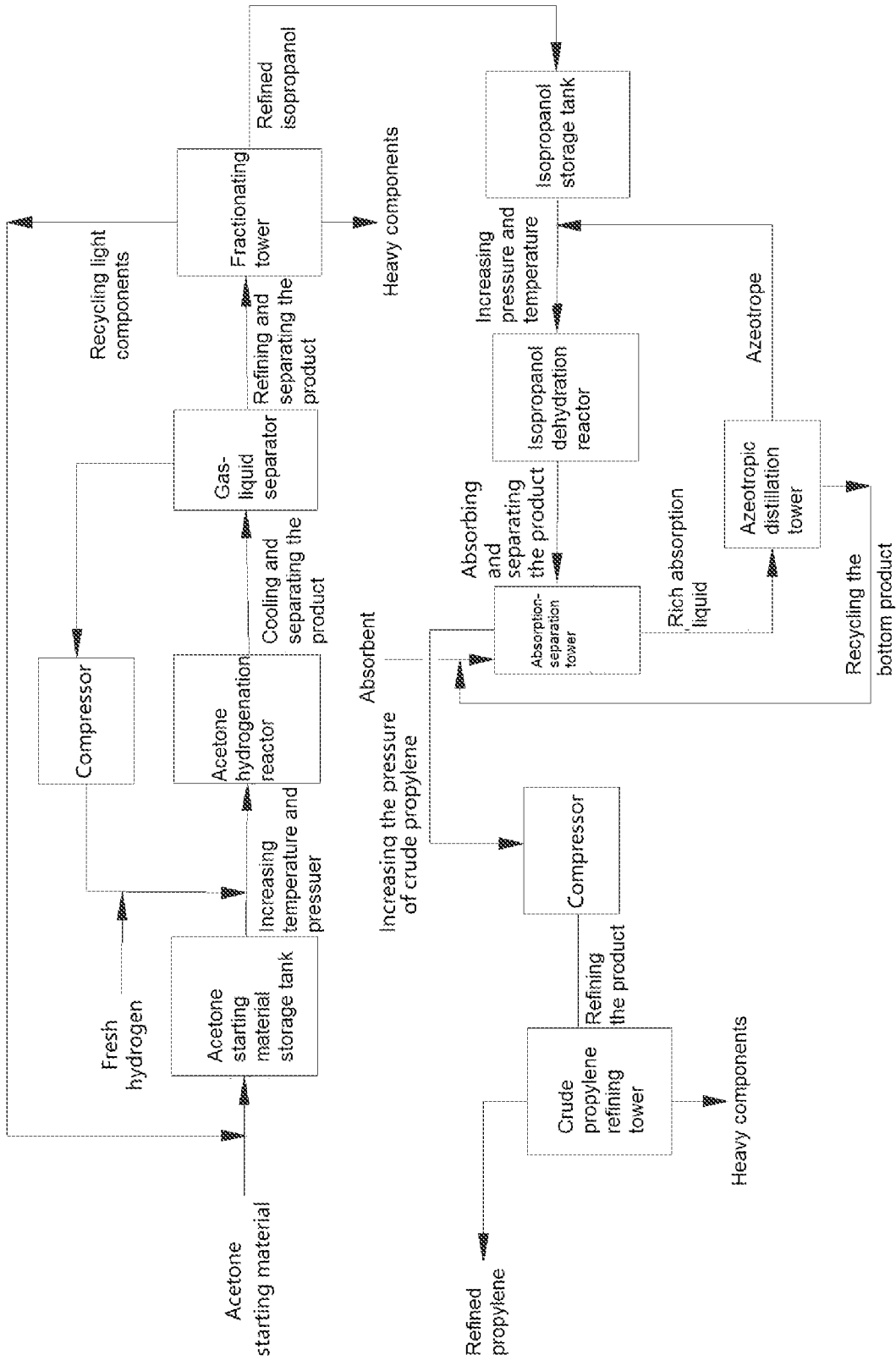

PREPARATION METHOD AND PRODUCTION DEVICE FOR PROPYLENE

TECHNICAL FIELD

The present application belongs to the field of chemical industry, and relates to a process for producing propylene by dehydration of isopropanol, a method for producing propylene from acetone comprising said process, and a related plant.

BACKGROUND ART

In recent years, the demand for phenol worldwide has risen greatly, for example, the total phenol production capacity worldwide has increased to 1363.7 ten thousand tons/year in 2017, which is 47% higher than the total phenol energy worldwide in 2009. According to statistics, a plurality of newly built phenol-acetone plants have been put into production in the world in recent years, particularly in Asia and China. Current phenol production mainly employs cumene oxidation process, in which acetone is a coproduct. With the strong global demand of phenol, a problem is caused that the rigid supply of co-produced acetone in existing phenol-ketone plants is too large, and the situation of regional or even global acetone surplus will appear and even appears.

In view of the current situation of large production capacity, large market supply and demand and low price of acetone in China and even in the world, and the shortage and high price of propylene, the integration of a process for producing propylene by hydrogenating and dehydrating acetone with a phenol-ketone plant can be used to solve the problems of low acetone price and unsmooth sale, and provide a technical scheme for adjusting the product proportion for phenol-ketone plants, so that the market competitiveness of phenol and downstream products thereof can be remarkably improved, particularly in the period when there is large price difference between propylene and acetone, and a remarkable economic benefit can be obtained.

CN 102690172A discloses a method for producing isopropanol by hydrogenation of acetone, which aims to solve the problems encountered in generating isopropanol by hydrogenation of acetone and removing impurities, especially water, from isopropanol, and comprises converting acetone into isopropanol by hydrogenation, then removing water from the isopropanol by using diisopropylamine as an entrainer, and then removing heavy components, to obtain a qualified isopropanol product.

CN102728361A discloses a catalyst for producing isopropanol by hydrogenation of acetone and application thereof. The catalyst comprises alumina with a BET specific surface area of 150-359 $m^2/g$ and a pore volume of 0.30-0.8 $m^2/g$ as a carrier, and 8-25% of nickel with a surface area of 10-30 $m^2/g$ total nickel content.

CN103772145B discloses a separation method useful in the production of isopropanol by hydrogenation of acetone, comprising: performing azeotropic distillation and extractive distillation on the acetone hydrogenation product to obtain a high-purity isopropanol. The method specifically comprises the following steps: (1) feeding the acetone hydrogenation product into a rectifying tower for azeotropic distillation, withdrawing an azeotrope from the top of the tower, a heavy component from the bottom of the tower, and an isopropanol product from a side line of the tower; (2) passing the azeotrope withdrawn from the top of the rectifying tower to a recovery tower, subjecting it to extraction and rectification using an extracting agent, withdrawing a reflux of acetone and isopropanol from the top of the tower and returning it back to the reactor for recycle, and withdrawing a water solution rich in the extracting agent from the bottom of the tower; (3) sending the material from the bottom of the recovery tower to a dehydration tower, withdrawing the extracting agent from the bottom of the tower, and recycling to the recovery tower.

CN103508833B discloses a method for producing propylene by dehydration of isopropanol, comprising: contacting isopropanol with a catalyst under conditions for isopropanol dehydration reaction, to obtain propylene by dehydration of the isopropanol. The catalyst is prepared by the following method: preparing a gel system comprising a template and an aluminum source; then removing mesoporous nano-alumina.

Huixia Ma et al state, in "Thermodynamic analysis of reaction for producing propylene by dehydration of isopropanol", Modern Chemical Industry, volume 40, No. 6, that from the thermodynamic equilibrium perspective, the dehydration reaction of isopropanol is preferably conducted using a high-temperature atmospheric-pressure gas phase dehydration process. However, since the isopropanol dehydration reaction is still in a kinetic control stage and does not reach thermodynamic equilibrium, the above reference provides little guidance for conducting isopropanol dehydration reaction.

Chunyan Liu et al state, in "Reaction for producing propylene by dehydration of isopropanol catalyzed with an acidic catalyst", Petrochemical Industry, volume 19, No. 5, that a higher conversion rate of isopropanol can be achieved by simply increasing the reaction temperature, but the selectivity of propylene is reduced due to more side reactions, and the effect is not ideal.

DISCLOSURE OF THE INVENTION

The inventors of the present application believe that the hydrogenation of acetone to produce propylene is an excellent technical route for regulating the product scheme, in view of the situation that the demand of phenol on the market is strong and the co-production of acetone by a phenol-ketone plant is excessive. However, the process for producing propylene by hydrogenation of acetone in the prior art has the problems of long process flow, high requirements for conversion rate and selectivity of a catalyst, high energy consumption of a separation process, high requirement on product purity and the like, and the prior art also adopts single-stage process operation of acetone hydrogenation and isopropanol dehydration, and there is no integrated process for producing isopropanol by hydrogenation/dehydration from acetone, and for producing propylene from acetone, since the quality requirement (GB/T 7716-2014) for polymer grade propylene products is high, the following problems are encountered: (1) the single-stage conversion rate and selectivity requirements for acetone hydrogenation and isopropanol dehydration are high, otherwise if the conversion rate and selectivity of any stage are low, the quality requirement of propylene cannot be met; (2) especially for the process of producing propylene by dehydration of isopropanol, the single-stage conversion rate and selectivity directly influence the yield, product purity and energy consumption for refining and separation of propylene, so that the improvement of the conversion rate and selectivity of the process for producing propylene by dehydration of isopropanol is very important for improving the product purity of propylene, reducing the consumption of isopropanol and acetone, and reducing the energy consumption for separation and the like. Therefore, the improvement of the overall conversion rate and selectivity of the process for producing propylene from acetone, especially the conversion rate and selectivity of the process for producing propylene by dehydration of isopropanol, can not only improve the purity of propylene products, but also play an important role in reducing the separation energy consumption and raw material consumption of the whole process.

Therefore, the inventors of the present application believe that, in view of the situation of excessive acetone and shortage of propylene caused by the excessive supply of acetone co-production in current phenol-ketone plants, while no integrated process for producing propylene from acetone or integrated technology combining propylene production with phenol plant is present in the prior art, an integration of the process for producing propylene by hydrogenation of acetone and then dehydration with the phenol-ketone plant can not only solve the problems of low price and poor marketability of acetone, but also provide a technical scheme for adjusting the product proportion for phenol-ketone plants, and thus has obvious economic benefits.

After assiduous studying, the inventors of the present application have found that, in the dehydration reaction of isopropanol, besides the dehydration reaction of isopropanol for producing propylene, there is a significant side reaction in which propylene is dimerized to produce heavy component impurities such as propylene dimer, and that, in the case where the dehydration catalyst comprises alumina, the propylene dimer may also cleaved to produce impurities such as light carbon components such as ethylene and C4 heavy components such as butene, because of the high temperature required for the dehydration reaction. Therefore, in the process of producing propylene by dehydration of isopropanol, if the dehydration catalyst comprises alumina, the yield, product purity and energy consumption of purification and separation of propylene are directly influenced by the dimeric propylene and the cracked C2 and C4 components in the reaction product. Therefore, the quality of the produced propylene is reduced by impurities generated by side reactions, and the produced propylene needs to be further refined to meet the requirements of the national standard for polymer grade propylene.

The requirements on superior product and first-class product of the national standard GB/T7716-2014 "Propylene for polymerization-Specification" are shown in Table 1.

TABLE 1

Technical requirements for polymer grade propylene

| No. | Item | Superior product | First-class product | Qualified product | Test method |
|---|---|---|---|---|---|
| 1 | Propylene content φ/%≥ | 99.6 | 99.2 | 98.6 | GB/T 3392 |
| 2 | Alkane content φ/% | Report | Report | Report | GB/T 3392 |
| 3 | Ethylene content/(mL/m³)≤ | 20 | 50 | 100 | GB/T 3392 |
| 4 | Acetylene content/(mL/m³)≤ | 2 | 5 | 5 | GB/T 3394 |
| 5 | Methylacetylene + allene ≤ content/(mL/m³) | 5 | 10 | 20 | GB/T 3392 |
| 6 | Oxygen content/(mL/m³)≤ | 5 | 10 | 10 | GB/T 3396 |
| 7 | Carbon monoxide/(mL/m³)≤ | 2 | 5 | 5 | GB/T 3394 |
| 8 | Carbon dioxide/(mL/m³)≤ | 5 | 10 | 10 | GB/T 3394 |
| 9 | Butene + butadiene ≤ content/(mL/m³) | 5 | 20 | 20 | GB/T 3392 |
| 10 | Sulfur content/(mg/kg)≤ | 1 | 5 | 8 | GB/T 11141[a] |
| 11 | Water content/(mg/kg)≤ | 10[b] | | Agreed | GB/T 3727 |
| 12 | Methanol content/(mg/kg)≤ | 10 | | 10 | GB/T 12701 |
| 13 | Dimethyl ether ≤ content/(mg/kg)[c] | 2 | 5 | Report | GB/T 12701 |

[a]In case of disagreement, the UV fluorescence method described in GB/T 11141-2014 shall prevail.
[b]The index may also be determined by negotiation between the supply and demand parties.
[c]This item is only applicable to the process for producing olefin or propylene from methanol.

As can be seen from Table 1, the propylene content of the first-class product of polymer grade propylene is required to be ≥99.2 φ/%, the propylene content of the superior product is required to be ≥99.6 φ/%; though the propylene content of the superior product of national standard is merely required to be 99.6% or more, it is further required that, in the first-class product of national standard, the C2 ethylene content is 50 ppm or less, the acetylene content is 5 ppm or less, the content of C3-C4 unsaturated impurities is 10 ppm or less, and, in the superior product of national standard, the content of C2 unsaturated impurities is 20 ppm or less, and the content of C3-C4 unsaturated impurities is 5 ppm or less.

The inventors of the present application have also found that, because the content of light components such as ethylene and acetylene is strictly limited in the polymer grade propylene product, once light component impurities are generated in the dehydration reaction process, a light component removing column of about one hundred meters is needed to separate the light component impurities, which results in significant increase of energy consumption and material consumption in the subsequent separation process. How to directly control the light component impurities such as ethylene and acetylene in the effluent of isopropanol dehydration reaction within the content range required by the standard, reduce the energy consumption and material consumption of the subsequent separation and purification section, even completely omit the light component removing column, and obtain a polymer grade propylene product at lower cost is one of the main problems to be solved by the present application, which is also one of the technical problems existing in the prior art.

The inventors of the present application have further found through diligent studies that in an isopropanol dehydration reaction, if the dehydration catalyst comprises alumina, the reduction of impurity components can be achieved by suppressing the dimerization reaction of propylene and the cracking of the dimerization product by adding a small amount of water. Meanwhile, the inventors of the present application have also found that, in such an isopropanol dehydration reaction, there is a close correlation between the water content of the reaction starting material and the amount of specific impurities produced. Moreover, through a correlation formula under the condition of specific conversion rate, the controllable regulation of the amount of impurities generated can be realized by regulating and controlling the water content of the starting materials, so that the object of reducing impurities which are difficult to be separated in the isopropanol dehydration can be achieved. In addition, the correlation method for further regulating and controlling reaction impurities by regulating and controlling the water content of the starting materials can avoid the problem of the increase of side reaction caused by current operation for increasing the conversion rate of isopropanol by simply heating, guide the current industrial operation, simplify the reaction control means, effectively inhibit the dehydration side reaction of isopropanol and reduce the subsequent separation difficulty of propylene products. In addition, because water vapor would cause the removal of aluminum from the aluminum-containing catalyst, in turn damage the stability of the catalyst, the adverse effect on the catalyst under a larger water vapor atmosphere can be avoided, and the total energy consumption of the reaction can be reduced by controlling the water amount added in the reaction.

The present application has been completed based on the above findings.

Particularly, the present application relates to the following aspects.

1. A dehydration process, comprising a step of subjecting a starting material containing isopropanol to a dehydration reaction in the presence of a dehydration catalyst comprising alumina to produce a product containing propylene (referred to as dehydration step), wherein the starting material has a water content of 0.1 to 10.0 wt % (preferably 1.0 to 9.0 wt %, more preferably 3.0 to 5.0 wt %, relative to 100 wt % of the total mass of the starting material), and the product has a total content of C2 unsaturated impurities and C3-C4 unsaturated impurities of 80 ppm or less (preferably 75 ppm or less, 50 ppm or less, 40 ppm or less, 30 ppm or less, or 27 ppm or less, relative to 100 wt % of the total mass of the product).

2. The dehydration process according to any one of the preceding or subsequent aspects, wherein said product has a C2 unsaturated impurities content of 50 ppm or less (preferably 30 ppm or less, 25 ppm or less, or 22 ppm or less, relative to 100 wt % of the total mass of the product), and/or has a C3-C4 unsaturated impurities content of 30 ppm or less (preferably 20 ppm or less, 10 ppm or less, or 5 ppm or less, relative to 100 wt % of the total mass of the product), and/or has a propylene content of 65.0 to 69.8 wt % (preferably 66.0 to 69.5 wt %, relative to 100 wt % of the total mass of the product).

3. The dehydration process according to any one of the preceding or subsequent aspects, wherein said starting material has an isopropanol content of 90.0-99.9 wt % (preferably 91.0-99.0 wt %, more preferably 92.0-97.0 wt %, relative to 100 wt % of the total mass of said starting material) and/or the conversion rate of isopropanol is 96.0-99.9% (preferably 97.0-99.8%, more preferably 98.5-99.5%).

4. The dehydration process according to any one of the preceding or subsequent aspects, wherein said dehydration catalyst comprising alumina is selected from solid acid catalysts comprising alumina, preferably at least one selected from amorphous silica-alumina and molecular sieves, more preferably amorphous silica-alumina, particularly preferably amorphous silica-alumina having an alumina content of 1-30 wt % (preferably 1-15 wt %), with the balance being silica, more particularly preferably said amorphous silica-alumina having been subjected to a saturated steam treatment at 300-500° C.

5. The dehydration process according to any preceding or subsequent aspects, wherein the operating conditions of the dehydration step include: a reaction temperature of 150-450° C. (preferably 200-350° C.), a reaction pressure of 0.05-1.0 MPaG (preferably 0.1-0.5 MPaG), and a volume space velocity of 0.05-5.0 $h^{-1}$ (preferably 1-3 $h^{-1}$).

6. The dehydration process according to any one of the preceding or subsequent aspects, further comprising the step of separating an isopropanol/water mixture (preferably an azeotrope) from said product, or, further comprising the steps of:

1) washing the product with an absorbent, preferably at least one selected from the group consisting of water and isopropanol, especially water, to obtain a crude propylene product and a rich absorption liquid, 2) subjecting the crude propylene product to separation, preferably rectification, to remove heavy components, preferably only remove heavy components, to obtain refined propylene, and 3) subjecting the rich absorption liquid to separation, preferably rectification, to obtain an isopropanol/water mixture, preferably an azeotrope.

7. The dehydration process according to any preceding or subsequent aspects, wherein the mixture has a water content of 5-90 wt % (preferably 10-80 wt %, 10-50 wt % or 10-20 wt %, more preferably 12-13 wt %, relative to 100 wt % of the total mass of the mixture).

8. The dehydration process according to any one of the preceding or subsequent aspects, further comprising a step of recycling at least a portion (preferably 50 wt % or more, 80 wt % or more, 90 wt % or more, or substantially 100 wt %) of the mixture to the dehydration step (referred to as a recycling step).

9. The dehydration process according to any preceding or subsequent aspects, wherein in the recycling step, the at least a portion of the mixture is mixed with the starting material of the dehydration step, optionally supplemented with an additional amount of water, to adjust (e.g., increase or decrease) the water content of the staring material to a predetermined level.

10. The dehydration process according to any one of the preceding or subsequent aspects, further comprising the step of measuring the C3-C4 unsaturated impurities content of the product and comparing the measured value of the content (in ppm) with a preset value (such as 20 ppm, 10 ppm or 5 ppm, based on 100 wt % of the total mass of the product), wherein when the measured value of the content is greater than the preset value, the conversion rate of isopropanol is measured, to obtain a measured value (set as C, in %) of said conversion rate, 1) when the measured value C is between 96.0% and 99.0%, the water content of the starting material is increased (preferably by 0.01 to 30 times, 0.01 to 20 times, 0.01 to 10 times, 0.01 to 5 times, 0.01 to 1 time, 0.01 to 0.5 times, 0.01 to 0.3 times, 0.01 to 0.2 times, or 0.01 to 0.1 times), with a proviso that the water content after the increase is in a range of 0.1 to 3.0 wt % (relative to 100 wt % of the total mass of the starting material), preferably, when a planar rectangular coordinate system is established with the value of the conversion rate of isopropanol (in %) as an abscissa (with a starting point of 96.0 and an end point of 99.0), with the value of the water content of the starting material (in wt %) as an ordinate (with a starting point of 0.1 and an end point of 3.0) and with the coordinate (0, 0) as the origin point, a straight line segment is drawn from the coordinate (96.0, 0.1) to the coordinate (99.0, 3.0), and the coordinate of the measured value C on the straight line segment is set as (C, A1), where A1 represents the value of the water content corresponding to the measured value C on the straight line segment, a value in a range of A1 to 3.0 is selected as the value of the water content after the increase, preferably a value in a range of A1 to A1+(3.0−A1)/2 is selected as the value of the water content after the increase, 2) when the measured value C is between 99.0% and 99.5%, the water content of the starting material is increased (preferably by 0.01 to 2 times, 0.01 to 1 times, 0.01 to 0.5 times, 0.01 to 0.3 times, 0.01 to 0.2 times, or 0.01 to 0.1 times) with a proviso that the water content after the increase is in a range of 3.0 to 5.0 wt % (relative to 100 wt % of the total mass of the starting material), preferably, when a planar rectangular coordinate system is established with the value of the conversion rate of isopropanol (in %) as an abscissa (with a starting point of 99.0 and an end point of 99.5), with the value of the water content of the starting material (in wt %) as an ordinate (with a starting point of 3.0 and an end point of 5.0) and with the coordinate (0, 0) as the origin point, a straight line segment is drawn from the coordinate (99.0, 3.0) to the coordinate (99.5, 5.0), and the coordinate of the measured value C on the straight line segment is set as (C, A2), wherein A2 represents the value of the water content corresponding to the measured value C on the straight line segment, a value in a range of A2 to 5.0 is selected as the value of the water content after the increase, preferably a value in a range of A2 to A2+(5.0−A2)/2 is selected as the value of the water content after the increase, 3) when the measured value C is between 99.5% and 99.9%, the water content of the starting material is increased (preferably by 0.01 to 2 times, 0.01 to 1 times, 0.01 to 0.5 times, 0.01 to 0.3 times, 0.01 to 0.2 times, or 0.01 to 0.1 times) with a proviso that the water content after the increase is in a range of 5.0 to 10.0 wt % (preferably 5.0 to 9.0 wt %, relative to 100 wt % of the total mass of the starting material), preferably, when a planar rectangular coordinate system is established with the value of the conversion rate of isopropanol (in %) as an abscissa (with a starting point of 99.5 and an end point of 99.9), with the value of the water content of the starting material (in wt %) as an ordinate (with a starting point of 5.0 and an end point of 10.0) and with the coordinate (0, 0) as the origin point, a straight line segment is drawn from the coordinate (99.5, 5.0) to coordinate (99.9, 10.0), and the coordinate of the measured value C on the straight line segment is set as (C, A3), wherein A3 represents the value of the water content corresponding to the measured value C on the straight line segment, a value in a range of A3 to 10.0 (preferably A3 to 9.0) is selected as the value of the water content after the increase, preferably a value in a range of A3 to A3+(10.0−A3)/2 (preferably A3 to A3+(9.0−A3)/2) is selected as the value of the water content after the increase.

11. The dehydration process according to any one of the preceding or subsequent aspects, further comprising the step of measuring the C2 unsaturated impurities content of said product and comparing the measured value of the content (in ppm) with a preset value (for example 50 ppm, 30 ppm, 25 ppm or 22 ppm, relative to 100 wt % of the total mass of the product), wherein when the measured value of the content is greater than the preset value, the conversion rate of isopropanol is measured, to obtain a measured value (set as D, in %) of said conversion rate, 1) when the measured value D is between 96.0% and 99.0%, the water content of the starting material is increased (preferably by 0.01-50 times, 0.01-20 times, 0.01-10 times, 0.01-5 times, 0.01-1 time, 0.01-0.5 times, 0.01-0.3 times, 0.01-0.2 times, or 0.01-0.1 times), with a proviso that the water content after the increase is in a range of 0.1 to 5.0 wt % (relative to 100 wt % of the total mass of the starting material), preferably, when a planar rectangular coordinate system is established with the value of the conversion rate of isopropanol (in %) as an abscissa (with a starting point of 96.0, and an end point of 99.0), with the value of the water content of the starting material (in wt %) as an ordinate (with a starting point of 0.1, and an end point of 5.0), and with the coordinate (0, 0) as the origin point, a straight line segment is drawn from the coordinate (96.0, 0.1) to the coordinate (99.0, 5.0), and the coordinate of the measured value D on the straight line segment is set as (D, B1), wherein B1 represents the value of the water content corresponding to the measured value D on the straight line segment, a value in a range of B1 to 5.0 is selected as the value of the water content after the increase, preferably a value in a range of B1 to B1+(5.0−B1)/2 is selected as the value of the water content after the increase, 2) when the measured value D is between 99.0% and 99.9%, the water content of the starting material is increased (preferably by 0.01-3 times, 0.01-2 times, 0.01-1 time, 0.01-0.5 times, 0.01-0.3 times, 0.01-0.2 times, or 0.01-0.1 times) with a proviso that the water content after the increase is in a range of 5.0 to 10.0 wt % (preferably 5.0 to 9.0 wt %, relative to 100 wt % of the total mass of the starting material), preferably, when a planar rectangular coordinate system is established with the value of the conversion rate of isopropanol (in %) as an abscissa (with a starting point of 99.0 and an end point of 99.9), with the value of the water content of the starting material (in wt %) as an ordinate (with a starting point of 5.0 and an end point of 10.0) and with the coordinate (0, 0) as the origin point, a straight line segment is drawn from the coordinate (99.0, 5.0) to the coordinate (99.9, 10.0), and the coordinate of the measured value D on the straight line segment is set as (D, B2), wherein B2 represents the value of the water content corresponding to the measured value D on the straight line segment, a value in a range of B2 to 10.0 (preferably B2 to 9.0) is selected as the value of the water content after the increase, preferably a value in a range of B2 to B2+(10.0−B2)/2 (preferably B2 to B2+(9.0−B2)/2) is selected as the value of the water content after the increase.

12. A method for producing propylene, comprising the steps of:

subjecting acetone as a starting material to a hydrogenation reaction in the presence of a hydrogenation catalyst to produce a product containing isopropanol, separating the isopropanol-containing product to obtain a hydrogen-containing gas and an isopropanol-containing liquid, separating the isopropanol-containing liquid to obtain isopropanol, dehydrating the isopropanol to produce a propylene-containing product according to the dehydration process of any one of the preceding or subsequent aspects (referred to as dehydration step), washing the propylene-containing product with an absorbent to obtain a crude propylene product and a rich absorption liquid, separating the rich absorption liquid to obtain an isopropanol/water azeotrope, separating and removing heavy components from the crude propylene product to obtain refined propylene.

13. The method according to any one of the preceding or subsequent aspects, further comprising the steps of:

recycling at least a portion (preferably 50 wt % or more, 80 wt % or more, 90 wt % or more, or substantially 100 wt %) of the isopropanol/water azeotrope to the dehydration step.

14. A plant for producing propylene, comprising an acetone hydrogenation reactor, a hydrogenation product gas-liquid separator, a fractionating tower, an isopropanol dehydration reactor, a propylene absorption-separation tower, an azeotropic distillation tower and a crude propylene de-heavy fractionator connected in sequence, wherein the acetone hydrogenation reactor is configured to perform hydrogenation reaction on acetone used as a starting material in the presence of a hydrogenation catalyst to produce an isopropanol-containing product, the hydrogenation product gas-liquid separator is configured to separate the isopropanol-containing product to obtain a hydrogen-containing gas and an isopropanol-containing liquid, the fractionating tower is configured to separate the isopropanol-containing liquid to obtain isopropanol, the isopropanol dehydration reactor is configured to perform dehydration reaction on the isopropanol used as a starting material in the presence of an alumina-containing dehydration catalyst to produce a propylene-containing product, the propylene absorption-separation tower is configured to wash the propylene-containing product with an absorbent to obtain a crude propylene product and a rich absorption liquid, the azeotropic distillation tower is configured to separate the rich absorption liquid to obtain an isopropanol/water azeotrope, the crude propylene de-heavy fractionator is configured to separate and remove heavy components from the crude propylene product to obtain refined propylene, and a material outlet at the top and/or upper part of the azeotropic distillation tower is in communication with a material inlet of the isopropanol dehydration reactor.

15. The plant according to any one of the preceding or subsequent aspects, wherein at least two measurers, at least one comparator and at least one controller are provided at the product outlet of the isopropanol dehydration reactor, and in the at least two measurers, at least one is configured to measure the C3-C4 unsaturated impurities content and/or the C2 unsaturated impurities content of the product to obtain a measured value of the content, and at least one is configured to measure the conversion rate of isopropanol to obtain a measured value of the conversion rate, the at least one comparator is configured to compare the measured values with the preset values, and to issue instructions to said at least one controller based on the comparison result and said measured value of the conversion rate, the at least one controller is configured to execute the instructions to increase the water content of the starting material of the isopropanol dehydration reactor.

Alternatively, the present application also relates to the following aspects.

1. A method for the dehydration of isopropanol, characterized in that a reaction promoter is added during the dehydration reaction of isopropanol, and the reaction promoter is a mixture of an alkanol and water.

2. The method according to any one of the preceding or subsequent aspects, wherein the alkanol is at least one selected from isopropanol, n-propanol, methanol and ethanol.

3. The method according to any one of the preceding or subsequent aspects, characterized in that the content by mass of the alkanol in the mixture of the alkanol and water is 10 wt % to 90 wt %, preferably 50 wt % to 88 wt %.

4. The method according to any one of the preceding or subsequent aspects, characterized in that the reaction promoter is added in an amount of 0.01 to 15.0 wt %, preferably 1 to 10 wt %, more preferably 1.5 to 5.5 wt % of the isopropanol starting material.

5. The method according to any one of the preceding or subsequent aspects, characterized in that a catalyst is further added during the isopropanol dehydration reaction, and the catalyst is at least one selected from amorphous silica-alumina, ZSM-5 molecular sieve and resin catalyst.

6. The method according to any one of the preceding or subsequent aspects, characterized in that the conditions of the dehydration reaction of isopropanol include: a temperature of 150-450° C., a pressure of 0.05-1.0 MPaG, and a volume space velocity of the catalyst of 0.05-5.0 $h^{-1}$.

7. A process for producing propylene by dehydration of isopropanol, comprising the following reaction processes in sequence: an isopropanol dehydration reaction process, an isopropanol dehydration product absorption and separation process and a crude propylene refining process, wherein a reaction promoter is added during the isopropanol dehydration reaction process, and the reaction promoter is a mixture of an alkanol and water.

8. The process according to any one of the preceding or subsequent aspects, wherein the alkanol is at least one selected from isopropanol, n-propanol, methanol and ethanol.

9. The process according to any one of the preceding or subsequent aspects, wherein the content by mass of the alkanol in the mixture of the alkanol and water is from 10 wt % to 90 wt %.

10. The process according to any one of the preceding or subsequent aspects, wherein the reaction promoter is added in an amount of 0.01 to 15.0 wt % of the isopropanol starting material.

11. The process according to any one of the preceding or subsequent aspects, wherein the reaction promoter is an azeotrope of the alkanol and water.

12. The process according to any one of the preceding or subsequent aspects, characterized in that an absorbent is added during the absorption separation of the isopropanol dehydration product, wherein the absorbent is at least one selected from isopropanol, n-propanol, methanol, ethanol and water.

13. The process according to any one of the preceding or subsequent aspects, wherein the absorbent is water, isopropanol or a mixture of isopropanol and water at any ratio.
14. A process for producing propylene from acetone, comprising an acetone hydrogenation process, a hydrogenation product gas-liquid separation process, an isopropanol refining process in sequence, and the process for producing propylene by dehydration of isopropanol according to any one of the preceding or subsequent aspects.
15. The process according to any one of the preceding or subsequent aspects, wherein the alkanol is at least one selected from isopropanol, n-propanol, methanol and ethanol.
16. The process according to any one of the preceding or subsequent aspects, wherein the content by mass of the alkanol in the mixture of the alkanol and water is from 10 wt % to 90 wt %.
17. The process according to any one of the preceding or subsequent aspects, wherein the reaction promoter is added in an amount of 0.01 to 15.0 wt % of the isopropanol starting material.
18. The process according to any one of the preceding or subsequent aspects, wherein the reaction promoter is an azeotrope of the alkanol and water.
19. The process according to any one of the preceding or subsequent aspects, wherein the absorbent is at least one selected from isopropanol, n-propanol, methanol, ethanol and water.
20. The process according to any one of the preceding or subsequent aspects, characterized in that the hydrogenation of acetone is carried out under conditions including: a temperature of 100-200° C., a pressure of 0.5-6.0 MPaG, a volume space velocity of the catalyst of 0.05-15 $h^{-1}$, and a molar ratio of hydrogen to acetone of 2:1 to 15:1.
21. The process according to any one of the preceding or subsequent aspects, characterized in that, in the gas-liquid separation process of the acetone hydrogenation product, the gas obtained is hydrogen, which is recycled, and the liquid product comprises a small amount of unreacted acetone and heavy component byproducts, which are removed in a fractionating tower to obtain refined isopropanol.
22. A process system for producing propylene from acetone, comprising an acetone starting material storage tank, an acetone hydrogenation reactor, a gas-liquid separator, a fractionating tower, an isopropanol storage tank, an isopropanol dehydration reactor, an absorption-separation tower, a compressor and a crude propylene refining tower connected in sequence, wherein the absorption-separation tower is provided with an absorbent inlet, an outlet at the bottom of the tower is connected with an azeotropic distillation tower, and an azeotrope outlet of the azeotropic distillation tower is connected with an inlet of the isopropanol dehydration reactor.
23. The process system according to any one of the preceding or subsequent aspects, wherein the product outlet at the bottom of the azeotropic distillation tower is further connected to the inlet of the absorption-separation tower, and the product is added into the absorption-separation tower in parallel with the absorbent entering the absorption-separation tower.
24. The process system according to any one of the preceding or subsequent aspects, wherein a gas outlet of the gas-liquid separator is connected to a compressor and is finally connected to an acetone hydrogenation reactor, and hydrogen obtained by gas-liquid separation is used as make-up hydrogen for acetone hydrogenation.
25. The process system according to any one of the preceding or subsequent aspects, wherein the overhead light component product outlet of the fractionating tower is connected to an acetone starting material storage tank, and the acetone which is not completely reacted is recycled.
26. The process system according to any one of the preceding or subsequent aspects, wherein the acetone hydrogenation reactor is a tubular fixed bed reactor, in which a catalyst is filled in the tube, and a heat removal medium is introduced outside the tube.
27. The process system according to any one of the preceding or subsequent aspects, characterized in that the isopropanol dehydration reactor is a tubular fixed bed reactor, in which a catalyst is filled in the tube, and a heat supply medium is introduced outside the tube.

BRIEF DESCRIPTION OF THE DRAWINGS

The figure shows a schematic diagram of the process system for producing propylene from acetone according to the present application.

DETAILED DESCRIPTION OF THE INVENTION

The present application will be illustrated in detail hereinbelow with reference to embodiments thereof, but it should be noted that the scope of the present application is not limited by those embodiments, but is defined by the appended claims.

All publications, patent applications, patents, and other references cited herein are incorporated by reference in their entirety. Unless defined otherwise, all technical and scientific terms used herein have the same meaning as commonly understood by those skilled in the art. In case of conflict, the contents described herein, including definitions, should prevail.

Where a material, substance, method, step, device, component, or the like is described herein as "commonly known to those skilled in the art", "prior art" or the like, it is to be understood that said material, substance, method, step, device and component cover not only those conventionally used in the art at the time of filing the present application, but also those not commonly used at present but will become commonly known in the art to be suitable for a similar purpose.

In the context of the present application, unless specifically stated otherwise, all percentages, parts, ratios, etc. are expressed by weight and all pressures given are gauge pressures.

In the context of the present application, the C2 unsaturated impurities include ethylene and acetylene, and the C3-C4 unsaturated impurities include methylacetylene, propadiene, butenes, butadienes, diacetylenes, etc., especially methylacetylene, propadiene, butenes and butadiene.

In the context of the present application, the content of isopropanol (unreacted) in the product (in wt %) can be measured directly on-line by infrared spectroscopic analyzer on the gas at the outlet of the reactor, or can be analyzed by gas chromatography by condensing the reaction effluent at the outlet and taking the liquid after condensation and analyzing the isopropanol content (in wt %) in the liquid product by gas chromatography. In addition, the water content of the isopropanol starting material may be measured by sampling the starting material at the inlet of the reactor and measuring the water content of the starting material (in wt %) by gas chromatography or by using a moisture analyzer.

In the context of the present application, the isopropanol content A (in wt %) of the product is measured using an infrared spectroscopic analyzer and the water content B (in wt %) of the starting material is measured using a moisture analyzer, and the isopropanol conversion rate X is calculated as:

$$X=A/(1-B).$$

In the context of the present application, the isopropanol content C (in wt %) of the starting material, and the isopropanol content D (in wt %) of the product condensate, are measured by gas chromatography, the feed amount M (in g) of the starting material can be calculated by means of the pump flow rate and the sampling time, the mass N (in g) of the condensate can be obtained by weighing, and the conversion rate X of isopropanol is calculated according to the following equation:

$$X=(DN)/(CM).$$

In the context of the present application, any two or more embodiments of the present application may be arbitrarily combined, and the resulting technical solution forms a part of the initial disclosure of the present application and falls within the scope of the present application.

The endpoints of any numerical range and any numerical value described in the context of the present application is not restricted to the exact range or value, but should be interpreted to further encompass values close to said range or value. Moreover, regarding any numerical range described herein, arbitrary combinations can be made between the endpoints of the range, between each endpoint and any specific value within the range, or between any two specific values within the range, to provide one or more new numerical range(s), and said new numerical range(s) should also be deemed to have been specifically described in the present application.

According to an embodiment of the present application, it relates to a dehydration process, wherein the dehydration process is a process for producing propylene by dehydration of isopropanol.

According to an embodiment of the present application, the dehydration process comprises a step of subjecting an isopropanol-containing starting material to a dehydration reaction in the presence of a dehydration catalyst comprising alumina to produce a propylene-containing product, which is referred to as a dehydration step. According to the present application, the technical effect of the present application is particularly remarkable in the case where the dehydration catalyst comprises alumina.

According to an embodiment of the present application, the water content of the staring material is between 0.1 and 10.0 wt %, preferably between 1.0 and 9.0 wt %, more preferably between 3.0 and 5.0 wt %, relative to 100 wt % of the total mass of the starting material. According to the present application, when the water content is less than 0.1 wt %, the total content of the C2 unsaturated impurities and the C3-C4 unsaturated impurities in the product would exceed the upper limit of the numerical range specified in the present application, and the desired effect of the present application such as a significant reduction in the impurity content cannot be achieved. In addition, when the water content is higher than 10.0 wt %, not only the energy consumption of the dehydration process would increase, but also the total content of the C2 unsaturated impurities and the C3-C4 unsaturated impurities in the product would exceed the upper limit of the numerical range specified in the present application, and the desired effect of the present application such as a significant reduction in the impurity content cannot be achieved, either.

According to an embodiment of the present application, the sum of the content of C2 unsaturated impurities and the content of C3-C4 unsaturated impurities of the product is 80 ppm or less, preferably 75 ppm or less, 50 ppm or less, 40 ppm or less, 30 ppm or less or 27 ppm or less, relative to 100 wt % of the total mass of the product. Preferably, the product has a C2 unsaturated impurities content of 50 ppm or less, preferably 30 ppm or less, 25 ppm or less or 22 ppm or less, relative to 100 wt % of the total mass of the product. Preferably, the product has a C3-C4 unsaturated impurities content of 30 ppm or less, preferably 20 ppm or less, 10 ppm or less or 5 ppm or less, relative to 100 wt % of the total mass of the product.

According to an embodiment of the present application, the propylene content of the product is from 65.0 to 69.8% wt, preferably from 66.0 to 69.5% wt, relative to 100 wt % of the total mass of the product.

According to an embodiment of the present application, the isopropanol content of the starting material is 90.0-99.9 wt %, preferably 91.0-99.0 wt %, more preferably 92.0-97.0 wt %, relative to 100 wt % of the total mass of the starting material. In addition to isopropanol and water, the starting material may also contain other components such as those retaining from the acetone hydrogenation reaction, such as acetone or methanol and the like.

According to an embodiment of the present application, the conversion rate of isopropanol is 96.0 to 99.9%, preferably 97.0 to 99.8%, more preferably 98.5 to 99.5%, from the viewpoint of remarkably achieving the effect of the present application.

According to an embodiment of the present application, the dehydration catalyst can be any solid acid catalyst known in the art that is capable of dehydrating isopropanol, but must comprise alumina. The desired effect of the present application is most remarkable in the case where the dehydration catalyst comprises alumina. The dehydration catalyst is preferably at least one selected from amorphous silica-alumina and molecular sieves, more preferably amorphous silica-alumina. Here, as the amorphous silica-alumina, amorphous silica-alumina having an alumina content of 1 to 30% by mass (preferably 1 to 15% by mass), with the balance being silica, is particularly preferred. The amorphous silica-alumina may be commercially available or may be produced by a conventional method. More preferably, the amorphous silica-alumina is amorphous silica-alumina treated by saturated stream at 300-500° C. As an example of the method for producing the amorphous silica-alumina, it may comprise: taking commercially available amorphous silica-alumina pellets with a mass content of alumina of 1-15 wt %, and treating them for 5-10 hours at 300-500° C. in a saturated steam atmosphere. The catalyst has good dehydration activity, selectivity and long-period stability under very mild conditions in an isopropanol dehydration process. Further, as the dehydration catalyst, a core-shell type alumina catalyst described in CN102451674 can be also mentioned.

According to an embodiment of the present application, the reaction temperature of the dehydration step is 150-450° C., preferably 200-350° C.

According to an embodiment of the present application, the reaction pressure of the dehydration step is between 0.05 and 1.0 MPaG, preferably between 0.1 and 0.5 MPaG.

According to an embodiment of the present application, the volume space velocity of the dehydration step is between 0.05 and 5.0 $h^{-1}$, preferably between 1 and 3 $h^{-1}$.

According to an embodiment of the present application, the dehydration process further comprises the step of separating an isopropanol/water mixture from the product. Here, as the mixture, an azeotrope is preferable.

According to an embodiment of the present application, the dehydration process further comprises the steps of:

1) washing the product with an absorbent to obtain a crude propylene product and a rich absorption liquid. Here, the absorbent is a solvent capable of absorbing water-soluble components in the dehydration product of isopropanol, and is preferably water, isopropanol or a mixture of isopropanol and water at any ratio. The absorbent is a lean absorption liquid before being added, and becomes a rich absorption liquid after absorbing soluble components.
2) separating the crude propylene product to remove heavy components to obtain refined propylene. Here, as the separation, rectification is preferable. In addition, according to the present application, it is preferred that, since the content of light components in the crude propylene product obtained is very low due to the isopropanol dehydration process of the present application, a refined propylene product, particularly a refined propylene product meeting the requirements of the national polymer grade propylene, can be obtained by only removing heavy components from the crude propylene product by the separation. According to this preferred embodiment, the separation comprises only the step of removing heavy components, and does not need to comprise the step of removing light components, which is typically required in the prior art. As used herein, the "heavy component(s)" typically refers to hydrocarbon substances having four or more carbons, particularly the C4 unsaturated impurities, and the "light component(s)" typically refers to hydrocarbon substances having two or less carbons, particularly the C2 unsaturated impurities.
3) separating the rich absorption liquid to obtain an isopropanol/water mixture. Here, as the separation, rectification, particularly azeotropic rectification, is preferable.

According to an embodiment of the present application, in the dehydration process, the mixture has a water content of 5-90 wt %, preferably 10-80 wt %, 10-50 wt % or 10-20 wt %, more preferably 12-13 wt %, relative to 100 wt % of the total mass of the mixture.

According to an embodiment of the present application, it further comprises a step of recycling at least a portion of said mixture to said dehydration step (referred to as recycling step). Here, as the at least a portion, it is preferably 50 wt % or more, 80 wt % or more, 90 wt % or more, or substantially 100 wt % (i.e., substantially all is recycled). By recycling the mixture, in particular the azeotrope, to the dehydration step, the water content of the starting material can be flexibly adjusted and the overall energy consumption of the dehydration process can be significantly reduced. To this end, it is preferred that in the recycling step, the at least a portion of the mixture is mixed with the starting material of the dehydration step, optionally supplemented with an additional amount of water, to adjust (e.g., increase or decrease) the water content of the staring material to a predetermined level. Here, the present application has no particular limitation to the manner of mixing the mixture with the starting material (optionally including the additional amount of water), as long as these materials are sufficiently mixed. From the standpoint of adjusting the water content of the staring material, these materials are typically mixed prior to the dehydration reaction of the starting material (e.g., prior to entering a dehydration reactor).

The inventors of the present application have found that, in the reaction process, the water content of the isopropanol starting material is closely related to the conversion rate of isopropanol and the content of the C3-C4 unsaturated impurities or the C2 unsaturated impurities in the product. Specifically, when the reaction conversion rate exceeds 96%, for example, by increasing the reaction temperature, the content of the C3-C4 unsaturated impurities or the C2 unsaturated impurities in the reaction product increases significantly as the reaction conversion rate increases. To this end, the present application also relates to a scheme for controlling such impurities in the following embodiments.

According to an embodiment of the present application, the dehydration process further comprises the step of measuring the C3-C4 unsaturated impurities content of the product. The content may be measured, for example, by infrared spectroscopic analyzer. Typically, the measurement is performed at the reaction product outlet of the dehydration reactor. The measurement of the content may be performed continuously, intermittently, on-line, or off-line, and is not particularly limited.

According to this embodiment of the present application, by measuring the content, a measured value of the content (in ppm) is obtained. Then, the measured value of the content is compared with a preset value of the content. Here, as the preset value, for example, 20 ppm, 10 ppm or 5 ppm (relative to 100 wt % of the total mass of the product) may be mentioned. The preset value represents the maximum level of C3-C4 unsaturated impurities in the reaction product acceptable to a person skilled in the art.

According to this embodiment of the present application, by said comparison, if the measured value of the content is greater than the preset value (trigger condition), the conversion rate of isopropanol is measured, to obtain a measured value of the conversion rate (set as C, in %). Typically, the measurement of the conversion rate is carried out at the reaction product outlet of the dehydration reactor. The measurement of the conversion rate may be performed continuously, intermittently, on-line, or off-line, and is not particularly limited. In addition, according to the present application, the measurement of the content and the measurement of the conversion rate may be performed simultaneously or sequentially in a certain order, and there is no particular limitation, but from the viewpoint of efficiency, the measurement of the conversion rate is normally performed when the trigger condition is satisfied.

According to this embodiment of the present application, when the measured value C is between 96.0% and 99.0%, the water content of the starting material is increased, with a proviso that the water content after the increase is in a range of 0.1-3.0 wt % (relative to 100 wt % of the total mass of the starting material). Here, as the magnitude of the increase (amplitude), it is typically 0.01 to 30 times, 0.01 to 20 times, 0.01 to 10 times, 0.01 to 5 times, 0.01 to 1 time, 0.01 to 0.5 times, 0.01 to 0.3 times, 0.01 to 0.2 times or 0.01 to 0.1 times. According to the present application, it is preferable that, when a planar rectangular coordinate system is established with the value of the conversion rate of isopropanol (in %) as an abscissa (with a starting point of 96.0 and an end point of 99.0), with the value of the water content of the starting material (in wt %) as an ordinate (with a starting point of 0.1 and an end point of 3.0), and with the coordinate (0, 0) as the origin point, a straight line segment is drawn from the coordinate (96.0, 0.1) to the coordinate (99.0, 3.0), and the coordinate of the measured value C on the straight line segment is set as (C, A1), wherein A1 represents the value of the water content corresponding to the measured value C on the straight line segment, and a value in a range of A1 to 3.0 is selected as the value of the water content after the increase, preferably a value in a range of A1 to A1+(3.0−A1)/2 is selected as the value of the water content after the increase. As the value of the water content after the increase, A1 or its vicinity is typically selected. According to the present application, the content of the C3-C4 unsaturated impurities in the reaction product can be controlled to 10 ppm or less, preferably 5 ppm or less, by this control scheme, for example, when the conversion rate of isopropanol is changed by changing the reaction temperature (e.g., raising the reaction temperature).

According to this embodiment of the present application, when the measured value C is between 99.0% and 99.5%, the water content of the starting material is increased, with a proviso that the water content after the increase is in a range of 3.0-5.0 wt % (relative to 100 wt % of the total mass of the starting material). Here, as the magnitude of the increase (amplitude), it is typically 0.01 to 2 times, 0.01 to 1 time, 0.01 to 0.5 times, 0.01 to 0.3 times, 0.01 to 0.2 times or 0.01 to 0.1 times. According to the present application, it is preferable that, when a planar rectangular coordinate system is established with the value of the conversion rate of isopropanol (in %) as an abscissa (with a starting point of 99.0 and an end point of 99.5), with the value of the water content of the starting material (in wt %) as an ordinate (with a starting point of 3.0 and an end point of 5.0) and with the coordinate (0, 0) as the origin point, a straight line segment is drawn from the coordinate (99.0, 3.0) to the coordinate (99.5, 5.0), and the coordinate of the measured value C on the straight line segment is set as (C, A2), wherein A2 represents the value of the water content corresponding to the measured value C on the straight line segment, and a value in a range of A2 to 5.0 is selected as the value of the water content after the increase, preferably a value in a range of A2 to A2+(5.0−A2)/2 is selected as the value of the water content after the increase. As the value of the water content after the increase, A2 or its vicinity is typically selected. According to the present application, the content of the C3-C4 unsaturated impurities in the reaction product can be controlled to 10 ppm or less, preferably 5 ppm or less, by this control scheme, for example, when the conversion rate of isopropanol is changed by changing the reaction temperature (e.g., raising the reaction temperature).

According to this embodiment of the present application, when the measured value C is between 99.5% and 99.9%, the water content of the starting material is increased, with a proviso that the water content after the increase is in a range of 5.0-10.0 wt % (preferably 5.0-9.0 wt %, relative to 100 wt % of the total mass of the starting material). Here, as the magnitude of the increase (amplitude), it is typically 0.01 to 2 times, 0.01 to 1 time, 0.01 to 0.5 times, 0.01 to 0.3 times, 0.01 to 0.2 times or 0.01 to 0.1 times. According to the present application, it is preferable that, when a planar rectangular coordinate system is established with the value of the conversion rate of isopropanol (in %) as an abscissa (with a starting point of 99.5 and an end point of 99.9), with the water content of the starting material (in wt %) as the ordinate (with a starting point of 5.0 and an end point of 10.0), and with the coordinate (0, 0) as the origin point, a straight line segment is drawn from the coordinate (99.5, 5.0) to the coordinate (99.9, 10.0), and the coordinate of the measured value C on the straight line segment is set as (C, A3), wherein A3 represents the value of the water content corresponding to the measured value C on the straight line segment, a value in a range of A3 to 10.0 (preferably A3 to 9.0) is selected as the value of the water content after the increase, preferably a value in a range of A3 to A3+(10.0−A3)/2 (preferably A3 to A3+(9.0−A3)/2) is selected as the value of the water content after the increase. As the value of the water content after the increase, A3 or its vicinity is typically selected. According to the present application, the content of the C3-C4 unsaturated impurities in the reaction product can be controlled to 10 ppm or less, preferably 5 ppm or less, by this control scheme, for example, when the conversion rate of isopropanol is changed by changing the reaction temperature (e.g., raising the reaction temperature).

According to an embodiment of the present application, the dehydration process further comprises the step of measuring the C2 unsaturated impurities content of the product. The content may be measured, for example, by infrared spectroscopic analyzer. Typically, the measurement is performed at the reaction product outlet of the dehydration reactor. The measurement of the content may be performed continuously, intermittently, on-line, or off-line, and is not particularly limited.

According to this embodiment of the present application, by measuring the content, a measured value of the content (in ppm) is obtained. Then, the measured value of the content is compared with a preset value of the content. Here, as the preset value, for example, 50 ppm, 30 ppm, 25 ppm or 22 ppm (relative to 100 wt % of the total mass of the product) may be mentioned. The preset value represents the maximum level of C2 unsaturated impurities (typically ethylene+acetylene) in the reaction product acceptable to a person skilled in the art, for example 20 ppm of ethylene, 2 ppm of acetylene.

According to this embodiment of the present application, by said comparison, if the measured value of the content is greater than the preset value (trigger condition), the conversion rate of isopropanol is measured, to obtain a measured value of the conversion rate (set as D, in %). Typically, the measurement of the conversion rate is carried out at the reaction product outlet of the dehydration reactor. The measurement of the conversion may be performed continuously, intermittently, on-line, or off-line, and is not particularly limited. In addition, according to the present application, the measurement of the content and the measurement of the conversion rate may be performed simultaneously or sequentially in a certain order, and there is no particular limitation, but from the viewpoint of efficiency, the measurement of the conversion rate is typically performed when the trigger condition is satisfied.

According to this embodiment of the present application, when the measured value D is between 96.0% and 99.0%, the water content of the starting material is increased, with a proviso that the water content after the increase is in a range of 0.1-5.0 wt % (relative to 100 wt % of the total mass of the starting material). Here, as the magnitude of the increase (amplitude), it is typically 0.01 to 50 times, 0.01 to 20 times, 0.01 to 10 times, 0.01 to 5 times, 0.01 to 1 time, 0.01 to 0.5 times, 0.01 to 0.3 times, 0.01 to 0.2 times or 0.01 to 0.1 times. According to the present application, it is preferable that, when a planar rectangular coordinate system is established with the value of the conversion rate of isopropanol (in %) as an abscissa (with a starting point of 96.0 and an end point of 99.0), with the value of the water content of the starting material (in wt %) as an ordinate, and with the coordinate (0, 0) as the origin point, a straight line segment is drawn from the coordinate (96.0, 0.1) to the coordinate (99.0, 5.0), and the coordinate of the measured value D on the straight line segment is set as (D, B1), wherein B1 represents the value of the water content corresponding to the measured value D on the straight line segment, a value in a range of B1 to 5.0 is selected as the value of the water content after the increase, and preferably a value in a range of B1 to B1+(5.0−B1)/2 is selected as the value of the water content after the increase. As the value of the water content after the increase, B1 or its vicinity is typically selected. According to the present application, the content of ethylene impurities in the reaction product can be controlled to 20 ppm or less, and the content of acetylene in the reaction product can be controlled to 2 ppm or less, by this control scheme, for example, when the conversion rate of isopropanol is changed by changing the reaction temperature (for example, raising the reaction temperature).

According to this embodiment of the present application, when the measured value D is between 99.0% and 99.9%, the water content of the starting material is increased, with a proviso that the water content after the increase is in a range of 5.0-10.0 wt % (preferably 5.0-9.0 wt %, relative to 100 wt % of the total mass of the starting material). Here, as the magnitude of the increase (amplitude), it is typically 0.01 to 3 times, 0.01 to 2 times, 0.01 to 1 time, 0.01 to 0.5 times, 0.01 to 0.3 times, 0.01 to 0.2 times or 0.01 to 0.1 times. According to the present application, it is preferable that, when a planar rectangular coordinate system is established with the value of the conversion rate of isopropanol (in %) as an abscissa (with a starting point of 99.0 and an end point of 99.9), with the water content of the starting material (in wt %) as an ordinate (with a starting point of 5.0 and an end point of 10.0), and with the coordinate (0, 0) as the origin point, a straight line segment is drawn from the coordinate (99.0, 5.0) to the coordinate (99.9, 10.0), and the coordinate of the measured value D on the straight line segment is set as (D, B2), wherein B2 represents the value of the water content corresponding to the measured value D on the straight line segment, a value in a range of B2 to 10.0 (preferably B2 to 9.0) is selected as the value of the water content after the increase, and preferably a value in a range of B2 to B2+(10.0−B2)/2 (preferably B2 to B2+(9.0−B2)/2) is selected as the value of the water content after the increase. As the value of the water content after the increase, B2 or its vicinity is typically selected. According to the present application, the content of ethylene impurities in the reaction product can be controlled to 20 ppm or less, and the content of acetylene in the reaction product can be controlled to 2 ppm or less, by this control scheme, for example, when the conversion rate of isopropanol is changed by changing the reaction temperature (for example, raising the reaction temperature).

According to an embodiment of the present application, it also relates to a method for producing propylene, comprising the steps of:
subjecting acetone as a starting material to a hydrogenation reaction in the presence of a hydrogenation catalyst to produce a product containing isopropanol,
separating the isopropanol-containing product to obtain a hydrogen-containing gas and an isopropanol-containing liquid,
separating the isopropanol-containing liquid to obtain isopropanol,
subjecting the isopropanol to a dehydration reaction to produce a propylene-containing product according to the dehydration process of any one of the aspects described hereinabove (referred to as dehydration step),
washing the propylene-containing product with an absorbent to obtain a crude propylene product and a rich absorption liquid,
separating the rich absorption liquid to obtain an isopropanol/water azeotrope,
separating and removing heavy components from the crude propylene product to obtain refined propylene.

According to an embodiment of the present application, the hydrogenation of acetone may be carried out in any manner known in the art. For example, the hydrogenation of acetone may be carried out in the presence of an acetone hydrogenation catalyst, and any catalyst capable of hydrogenating acetone into isopropanol can be used, but preferably from the aspects of production cost, applicability and the like, a nickel-based catalyst or a copper-based catalyst is typically used, wherein the nickel content of the nickel-based catalyst is typically 5-45 wt %, and other active components or auxiliary components may also be comprised, and the copper content of the copper-based catalyst is typically 8-45 wt %, and other active components or auxiliary components may also be comprised. Further preferably, the copper-based catalyst has good hydrogenation activity and selectivity under very mild conditions in the process for producing isopropanol by hydrogenation of acetone is used, so that the energy consumption and material consumption of the whole plant are low. In addition, generally speaking, in the acetone hydrogenation process, the reaction temperature is 100-200° C., the reaction pressure is 0.5-6.0 MPaG, the volume space velocity of the catalyst is 0.05-15 $h^{-1}$, and the molar ratio of hydrogen to acetone is 2:1 to 15:1.

According to the present application, the isopropanol-containing product is separated to obtain a hydrogen-containing gas and an isopropanol-containing liquid. Here, the gas can be recycled, and the liquid comprises a small amount of unreacted acetone and heavy component byproducts, and the liquid is passed to a fractionating tower for impurities removal to obtain refined isopropanol. According to the present application, there is no limitation on the separation and removal, etc., and knowledge known in the art can be directly applied.

According to an embodiment of the present application, the method further comprises the steps of: recycling at least a portion of the isopropanol/water azeotrope to the dehydration step. Here, as the at least a portion, it is preferably 50 wt % or more, 80 wt % or more, 90 wt % or more, or substantially 100 wt % (i.e., substantially all is recycled).

According to an embodiment of the present application, it further relates to a plant for producing propylene, comprising an acetone hydrogenation reactor, a hydrogenation product gas-liquid separator, a fractionating tower, an isopropanol dehydration reactor, a propylene absorption-separation tower, an azeotropic distillation tower and a crude propylene de-heavy fractionator connected in sequence. Here, the propylene plant is a plant specifically used for carrying out the method for producing propylene of the present application described above.

According to an embodiment of the present application, in the plant for producing propylene, the acetone hydrogenation reactor is configured to perform hydrogenation reaction on acetone used as a starting material in the presence of a hydrogenation catalyst to produce an isopropanol-containing product, the hydrogenation product gas-liquid separator is configured to separate the isopropanol-containing product to obtain a hydrogen-containing gas and an isopropanol-containing liquid, the fractionating tower is configured to separate the isopropanol-containing liquid to obtain isopropanol, the isopropanol dehydration reactor is configured to perform dehydration reaction on the isopropanol used as a starting material in the presence of an alumina-containing dehydration catalyst to produce a propylene-containing product, the propylene absorption-separation tower is configured to wash the propylene-containing product with an absorbent to obtain a crude propylene product and a rich absorption liquid, the azeotropic distillation tower is configured to separate the rich absorption liquid to obtain an isopropanol/water azeotrope, the crude propylene de-heavy fractionator is configured to separate and remove heavy components from the crude propylene product to obtain refined propylene. According to the present application, it is not necessary to provide a tower for removing light components to obtain refined propylene.

According to an embodiment of the present application, in the plant for producing propylene, a material outlet at the top and/or upper part of the azeotropic distillation tower is in communication with a material inlet of the isopropanol dehydration reactor. By this particular communicating structure, it is possible to achieve a recycling of at least a portion of the isopropanol/water azeotrope to the dehydration step.

According to an embodiment of the present application, in the plant for producing propylene, a bottom liquid outlet of the azeotropic distillation tower is in communication with an absorbent inlet of the propylene absorption-separation tower.

According to an embodiment of the present application, the acetone hydrogenation reactor is a fixed bed reactor, preferably a tubular fixed bed reactor, and because the acetone hydrogenation reaction has a violent heat release, a catalyst is filled in the tube, and a heat removal medium is introduced outside the tube.

According to an embodiment of the present application, the isopropanol dehydration reactor is a fixed bed reactor, preferably, a tubular fixed bed reactor. Since the dehydration of isopropanol is an endothermic reaction, a catalyst is filled in the tube, and a heat supply medium is introduced outside the tube.

According to an embodiment of the present application, in the plant for producing propylene, at least two measurers, at least one comparator and at least one controller are provided at the product outlet of the isopropanol dehydration reactor, and in the at least two measurers, at least one is configured to measure the C3-C4 unsaturated impurities content and/or the C2 unsaturated impurities content of the product to obtain a measured value of the content, and at least one is configured to measure the conversion rate of isopropanol to obtain a measured value of the conversion rate (such as the measured value C or the measured value D described hereinbefore). In addition, the at least one comparator is configured to compare the measured value of the content with a preset value and to issue an instruction to the controller, preferably for implementing the impurity control scheme as described hereinbefore, based on the comparison result (e.g. the measured value of the content is greater than the preset value) and the measured value of the conversion rate, and the instruction is typically to increase the water content of the starting material of the isopropanol dehydration reactor in accordance with the impurity control scheme. Moreover, the controller is configured to execute the instruction to practically increase the water content of the staring material of the isopropanol dehydration reactor. For example, the controller may be provided on the circulation line of the azeotrope to increase the circulation ratio of the azeotrope, or on the water replenishing line to increase the amount of make-up water to the starting material.

Without being bound by any theory, the inventors of the present application believe that, in the dehydration reaction of isopropanol, when the dehydration catalyst comprises alumina, the dimerization of propylene to a propylene dimer such as 4 methyl-1 pentene and the like and the cleavage of the dimer to C2 and C4 olefin and alkyne components are promoted due to the presence of the B acid site on the dehydration catalyst. By comprising a small amount of water (e.g., more than 0.1 wt %,) in the starting material as a reaction competitor of the nucleophilicity of the B acid site, the present application can realize a competition with the two side reactions of propylene dimerization and cracking of dimerization product, thereby inhibiting the occurrence of the side reactions, while maintaining the reaction efficiency. However, when the water content is too high (e.g., more than 10.0 wt %), as the dehydration catalyst is susceptible to hydrolysis, and the like, causing an increase of the B acid site, the side reaction may be aggravated instead. In addition, the present application identifies the association between the water content and the heavy component and light component after the reaction, thereby facilitating an operation with predictability during the reaction process, avoiding the influence of blind operation on the generation of impurities and simultaneously realizing an effective inhibition of the impurity content under conditions capable of providing a high conversion rate of isopropanol.

EXAMPLES

The present application will be further illustrated in detail with reference to the following examples and comparative examples, but the present application is not limited to those examples.

Example 1

This example provides a process system for producing propylene from acetone:

As shown in the figure, the process system comprises an acetone starting material storage tank, an acetone hydrogenation reactor, a gas-liquid separator, a fractionating tower, an isopropanol storage tank, an isopropanol dehydration reactor, an absorption-separation tower, a compressor and a crude propylene refining tower, connected in sequence, wherein an outlet at the top of the absorption-separation tower is connected with the compressor, an outlet at the bottom of the absorption-separation tower is connected with an azeotropic distillation tower, an azeotrope outlet of the azeotropic distillation tower is connected with an inlet of the isopropanol dehydration reactor, and an outlet at the bottom of the azeotropic distillation tower is connected with an inlet of the absorption-separation tower, in parallel with an absorbent entering the absorption-separation tower; a gas outlet of the gas-liquid separator is connected to a compressor and finally connected to an acetone hydrogenation reactor, and hydrogen obtained by gas-liquid separation is used as make-up hydrogen for acetone hydrogenation; and a light component product outlet at the top of the fractionating tower is connected to an acetone starting material storage tank, and the acetone which is not completely reacted is recycled.

The acetone hydrogenation reactor is a tubular reactor, in which an acetone hydrogenation catalyst is filled in the tube, and a heat removing medium is introduced outside the tube to remove reaction heat in time. The isopropanol dehydration reactor is a tubular reactor, in which an isopropanol dehydration catalyst is filled in the tube, and a heat supply medium is introduced outside the tube to provide heat.

The method for producing propylene from acetone using the above process system is divided into an acetone hydrogenation section and an isopropanol dehydration section.

Acetone hydrogenation section: the acetone starting material is passed to the acetone starting material storage tank, of which the pressure is increased, the acetone starting material is mixed with circulating hydrogen and heated, and then the mixture is fed to an acetone hydrogenation reactor for hydrogenation reaction in the presence of an acetone hydrogenation catalyst to obtain a reaction effluent containing isopropanol. The reaction effluent is condensed and cooled and then passed to a gas-liquid separator, the separated gas is pressurized by a compressor and then recycled, and the separated liquid is passed to the fractionating tower. The mixture containing isopropanol is fractionated in the fractionating tower to remove the small amount of light components and heavy components to obtain refined isopropanol, wherein the removed light components are typically unreacted acetone and are recycled to the starting material tank, and the removed heavy components are typically acetone hydrogenation byproducts and can be continuously or intermittently discharged.

Isopropanol dehydration section: refined isopropanol obtained from the acetone hydrogenation section is used as a starting material and passed to the isopropanol storage tank, mixed with the azeotropic distillation product obtained in the azeotropic distillation tower and/or additionally added water, and then sent to the isopropanol dehydration reactor for isopropanol dehydration reaction in the presence of a dehydration catalyst to obtain a reaction effluent containing propylene, the reaction effluent is passed to the bottom of the absorption-separation tower, an absorbent is introduced into the top of the absorption-separation tower, after heat exchange and absorption mass transfer exchange in the tower, a crude propylene is discharged from the top of the tower and then pressurized in a compressor, and a rich absorption liquid is discharged from the bottom of the tower and passed to the azeotropic distillation tower. The crude propylene is passed to the crude propylene refining tower after being pressurized by the compressor, refined propylene and the small amount of heavy components are separated, wherein the heavy components are typically polymers of propylene, and the small amount of heavy components are discharged out intermittently. The rich absorption liquid passed to the azeotropic distillation tower undergoes azeotropic distillation in the tower to obtain an azeotrope at the top of the tower, and the bottom product of the tower is recycled as an absorbent to the absorption-separation tower for reuse.

The acetone starting material used in the following examples and comparative examples is available from a plant and its specifications are shown in Table 1.

TABLE 1

| Item | Index | Analytical standards/methods |
|---|---|---|
| Acetone content, wt % | ≥99.5 | GB/T 6026-2013 |
| Chroma/Hazen units | ≤5 | GB/T 3143-1982 |

TABLE 1-continued

| Item | Index | Analytical standards/methods |
|---|---|---|
| Density (20° C.)/(g/cm$^3$) | 0.789-0.791 | GB/T 4472-2011 |
| Evaporation residue, w/% | ≤0.002 | GB/T 6324.2-2004 |
| Water, w/% | ≤0.3 | GB/T 6283-2008 |
| Methanol, w/% | ≤0.05 | GB/T 6026-2013 |

Propylene was produced from acetone using the above-described system and method as follows:

Propylene was produced from the above-described acetone starting material:

wherein the size of the tube of the acetone hydrogenation reactor was φ20×2.0, the length of the tube was 1.5 meters, heat removal medium water was introduced outside the reaction tube, and heat was removed by vaporizing the water to generate 0.3 MPa steam. The conditions for acetone hydrogenation included: a temperature of 170° C., a pressure of 3.5 MPa, a space velocity of the catalyst of 1.5 h$^{-1}$, and a hydrogen-to-acetone volume ratio of 10:1. The acetone hydrogenation catalyst was a copper-based catalyst developed by Sinopec (Dalian) Research Institute of Petroleum and Petrochemicals Co., Ltd., and had a cylindrical shape.

Isopropanol was prepared by hydrogenation of acetone, and the isopropanol starting material was mixed with the rectification product obtained at the top of the azeotrope column and water, and then subjected to dehydration The size of the tube of the isopropanol dehydration reactor was φ10×2.0, and the conditions for isopropanol dehydration included: a temperature of 280° C., a pressure of 0.3 MPa, a space velocity of the catalyst of 1.5 h$^{-1}$, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape.

In the isopropanol dehydration section, the water content of the isopropanol starting material was 8 wt %, the isopropanol content in the product was 3.2 wt %, the content of C2 unsaturated impurities in the reaction effluent was 9 ppm, the content of C3-C4 unsaturated impurities in the reaction effluent was 3 ppm, and the conversion rate of isopropanol was 96.8%.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Example 2

The starting material and the method as described in Example 1 were employed to produce isopropanol, and the isopropanol and water were directly mixed and then used as the starting material for dehydration.

The size of the tube of the isopropanol dehydration reactor was φ10×2.0, and the conditions for isopropanol dehydration included: a temperature of 280° C., a pressure of 0.3 MPa, a space velocity of the catalyst of 1.5 h$^{-1}$, and an isopropanol dehydration catalyst that was a self-made alumina-based catalyst prepared as follows: amorphous silica-alumina pellets with an alumina content by mass of 10% were treated for 10 hours at a temperature of 450° C.

in a saturated steam atmosphere to obtain the isopropanol dehydration catalyst. The catalyst had a spherical shape.

In the isopropanol dehydration section, the water content of the isopropanol starting material was 0.5 wt %, the isopropanol content in the product was 2.0 wt %, the content of C2 unsaturated impurities in the reaction effluent was 40 ppm, the content of C3-C4 unsaturated impurities in the reaction effluent was 18 ppm, and the conversion rate of isopropanol was 98.0%.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Example 3

The starting material and the method as described in Example 1 were employed to produce isopropanol, and the isopropanol and water were directly mixed and then used as the starting material for dehydration.

The size of the tube of the isopropanol dehydration reactor was φ10×2.0, and the conditions for isopropanol dehydration included: a temperature of 280° C., a pressure of 0.3 MPa, a space velocity of the catalyst of 1.5 $h^{-1}$, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape.

In the isopropanol dehydration section, the water content of the isopropanol starting material was 2 wt %, the isopropanol content in the product was 2.3 wt %, the content of C2 unsaturated impurities in the reaction effluent was 21 ppm, the content of C3-C4 unsaturated impurities in the reaction effluent was 9 ppm, and the conversion rate of isopropanol was 97.7%.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Example 4

The starting material and the method as described in Example 1 were employed to produce isopropanol, the isopropanol and water were directly mixed and then used as the starting material for dehydration, and the isopropanol in the product was purified by extraction rectification for recycling.

The size of the tube of the isopropanol dehydration reactor was φ10×2.0, and the conditions for isopropanol dehydration included: a temperature of 280° C., a pressure of 0.3 MPa, a space velocity of the catalyst of 1.5 $h^{-1}$, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape.

In the isopropanol dehydration section, the water content of the isopropanol starting material was 8 wt %, the isopropanol content in the product was 3.1 wt %, the content of C2 unsaturated impurities in the reaction effluent was 4 ppm, the content of C3-C4 unsaturated impurities in the reaction effluent was 3 ppm, and the conversion rate of isopropanol was 96.9%.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Example 5

The starting material and the method as described in Example 1 were employed to produce isopropanol, and the isopropanol and water were directly mixed and then used as the starting material for dehydration.

The size of the tube of the isopropanol dehydration reactor was φ10×2.0, and the conditions for isopropanol dehydration included: a temperature of 280° C., a pressure of 0.3 MPa, a space velocity of the catalyst of 1.5 $h^{-1}$, and an isopropanol dehydration catalyst that was a self-made molecular sieve catalyst. The catalyst was clover-shaped.

In the isopropanol dehydration section, the water content of the isopropanol starting material was 8 wt %, the isopropanol content in the product was 2.8 wt %, the content of C2 unsaturated impurities in the reaction effluent was 10 ppm, the content of C3-C4 unsaturated impurities in the reaction effluent was 5 ppm, and the conversion rate of isopropanol was 97.2%.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Example 6

The starting material and the method as described in Example 1 were employed to produce isopropanol, and the isopropanol and water were directly mixed and then used as the starting material for dehydration.

The size of the tube of the isopropanol dehydration reactor was φ10×2.0, and the conditions for isopropanol dehydration included: a temperature of 280° C., a pressure of 0.3 MPa, a space velocity of the catalyst of 1.5 $h^{-1}$, a water content of the isopropanol starting material of 1%, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape.

During the operating of the plant, the reaction temperature was increased to maintain or increase the conversion rate of the reaction and to improve the reaction efficiency. The reaction temperature was increased to 290° C., and then a measurement was conducted, and according to the measurement, the methylacetylene and propadiene content in the gas product was 6 ppm, the butylene and butadiene content in the gas product was 7 ppm, the isopropanol content in the product was 2.5 wt %, and its conversion rate was 97.5%. After calculating according to the equation for adjusting the water content of the reconstituted material described in the present application, the water content of isopropanol in the starting material was adjusted to 1.5%, and according to a measurement conducted under such reaction conditions, in the reaction effluent, the content of C2 unsaturated impurities was 15 ppm, the methylacetylene and propadiene content was 5 ppm, and the butylene and butadiene content was 4 ppm.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Example 7

The starting material and the method as described in Example 1 were employed to produce isopropanol, and the isopropanol and water were directly mixed and then used as the starting material for dehydration.

The size of the tube of the isopropanol dehydration reactor was φ10×2.0, and the conditions for isopropanol dehydration included: a temperature of 290° C., a pressure of 0.3 MPa, a space velocity of the catalyst of 1.5 $h^{-1}$, a water content of the isopropanol starting material of 1%, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape.

During the operating of the plant, the reaction temperature was increased to maintain or increase the conversion rate of the reaction and to improve the reaction efficiency. The reaction temperature was increased to 290° C., and then a measurement was conducted, and according to the measurement, the ethylene content in the gas product was 23 ppm, the acetylene content in the gas product was 2 ppm, the isopropanol content in the product was 2.5 wt %, and its conversion rate was 97.5%. After calculating according to the equation for adjusting the water content described in the present application, the water content of isopropanol in the starting material was adjusted to 2.5%, and according to a measurement conducted under such reaction conditions, in the reaction effluent, the ethylene content was 14 ppm, the acetylene content was 1 ppm, the methylacetylene and propadiene content was 4 ppm, and the butene and butadiene content was 4 ppm.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Example 8

The starting material and the method as described in Example 1 were employed to produce isopropanol, and the isopropanol and water were directly mixed and then used as the starting material for dehydration.

The size of the tube of the isopropanol dehydration reactor was φ10×2.0, and the conditions for isopropanol dehydration included: a temperature of 280° C., a water content of the isopropanol starting material of 3.5%, a pressure of 0.3 MPa, a space velocity of the catalyst of 1.5 $h^{-1}$, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape.

During the operating of the plant, the reaction temperature was increased to maintain or increase the conversion rate of the reaction and to improve the reaction efficiency. The reaction temperature was increased to 301° C., and then a measurement was conducted, and according to the measurement, the methylacetylene and propadiene content in the gas product was 7 ppm, the butylene and butadiene content in the gas product was 8 ppm, the isopropanol content in the product was 0.7 wt %, and its conversion rate was 99.3%. After calculating according to the equation for adjusting the water content of the reconstituted material described in the present application, the water content of isopropanol in the starting material was adjusted to 4.2%, and according to a measurement conducted under such reaction conditions, in the reaction effluent, the content of C2 unsaturated impurities was 16 ppm, and the methylacetylene and propadiene content was 4 ppm, and the butylene and butadiene content was 5 ppm.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Example 9

The starting material and the method as described in Example 1 were employed to produce isopropanol, and the isopropanol and water were directly mixed and then used as the starting material for dehydration.

The size of the tube of the isopropanol dehydration reactor was φ10×2.0, and the conditions for isopropanol dehydration included: a temperature of 280° C., a water content of the isopropanol starting material of 3.5%, a pressure of 0.3 MPa, a space velocity of the catalyst of 1.5 $h^{-1}$, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape.

During the operating of the plant, the reaction temperature was increased to maintain or increase the conversion rate of the reaction and to improve the reaction efficiency. The reaction temperature was increased to 301° C., and then a measurement was conducted, and according to the measurement, the ethylene content in the gas product was 22 ppm, the acetylene content in the gas product was 2 ppm, the isopropanol content in the product was 0.7 wt %, and its conversion rate was 99.3%. After calculating according to the equation for adjusting the water content described in the present application, the water content of isopropanol in the starting material was adjusted to 6.6%, and according to a measurement conducted under such reaction conditions, in the reaction effluent, the ethylene content was 18 ppm, the acetylene content was 1 ppm, the methylacetylene and propadiene content was 4 ppm, and the butene and butadiene content was 4 ppm.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Example 10

The starting material and the method as described in Example 1 were employed to produce isopropanol, and the isopropanol and water were directly mixed and then used as the starting material for dehydration.

The size of the tube of the isopropanol dehydration reactor was φ10×2.0, and the conditions for isopropanol dehydration included: a temperature of 280° C., a water content of the isopropanol starting material of 7.0%, a pressure of 0.2 MPa, a space velocity of the catalyst of 1.5 $h^{-1}$, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape.

During the operating of the plant, the reaction temperature was increased to maintain or increase the conversion rate of the reaction and to improve the reaction efficiency. The reaction temperature was increased to 308° C., and then a measurement was conducted, and according to the measurement, the methylacetylene and propadiene content in the gas product was 7 ppm, the butylene and butadiene content in the gas product was 6 ppm, the isopropanol content in the product was 0.3 wt % and its conversion rate was 99.7%. After calculating according to the equation for adjusting the water content of the reconstituted material described in the present application, the water content of isopropanol in the starting material was adjusted to 8.7%, and according to a measurement conducted under such reaction conditions, in the reaction effluent, the content of C2 unsaturated impurities was 21 ppm, the methylacetylene and propadiene content was 3 ppm, and the butylene and butadiene content was 5 ppm.

The properties of the final propylene product, the selectivity of the isopropanol dehydration catalyst, the composition of unsaturated hydrocarbon impurities in the product and the energy consumption (energy consumption refers to the energy consumption per ton of product of the whole process when a qualified propylene product is produced by dehydration of isopropanol) are shown in Table 2.

Comparative Example 1

Pure isopropanol was used as a starting material and fed to a reactor for dehydration, and the size of the tube of the isopropanol dehydration reactor was φ10×2.0.

The conditions for isopropanol dehydration included: a temperature of 280° C., a pressure of 0.3 MPa, a space velocity of the catalyst of 1.5 $h^{-1}$, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape and the product was analyzed by gas chromatography.

Here, the water content of the isopropanol starting material was 0 wt %, and the isopropanol content in the product was 0.9 wt %.

The properties of the final propylene product, the conversion rate of isopropanol, the composition of alkene and alkyne impurities in the product and the energy consumption (energy consumption refers to the energy consumption per ton of product of the whole process when a qualified propylene product is produced by dehydration of isopropanol) are shown in Table 2.

Comparative Example 2

Pure isopropanol was used as a starting material and fed to a reactor for dehydration, and the size of the tube of the isopropanol dehydration reactor was φ10×2.0.

The conditions for isopropanol dehydration included: a temperature of 300° C., a pressure of 0.3 MPa, a space velocity of the catalyst of 1.5 $h^{-1}$, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape and the product was analyzed by gas chromatography.

Here, the water content of the isopropanol starting material was 0% by weight, and the isopropanol content of the product was 0.3% by weight.

The properties of the final propylene product, the conversion rate of isopropanol, the composition of alkene and alkyne impurities in the product and the energy consumption (energy consumption refers to the energy consumption per ton of product of the whole process when a qualified propylene product is produced by dehydration of isopropanol) are shown in Table 2.

Comparative Example 3

Pure isopropanol was used as a starting material and fed to a reactor for dehydration, and the size of the tube of the isopropanol dehydration reactor was φ10×2.0.

The conditions for isopropanol dehydration included: a temperature of 330° C., a pressure of 0.3 MPa, a space velocity of the catalyst of 1.5 $h^{-1}$, and an isopropanol dehydration catalyst that was a self-made alumina-based catalyst prepared as follows: amorphous silica-alumina pellets with an alumina content by mass of 10% were treated for 10 hours at a temperature of 450° C. in a saturated steam atmosphere to obtain the isopropanol dehydration catalyst. The catalyst had a spherical shape and the product was analyzed by gas chromatography.

Here, the water content of the isopropanol starting material was 16 wt %, and the isopropanol content of the product was 0.5 wt %.

The properties of the final propylene product, the conversion rate of isopropanol, the composition of alkene and alkyne impurities in the product and the energy consumption (energy consumption refers to the energy consumption per ton of product of the whole process when a qualified propylene product is produced by dehydration of isopropanol) are shown in Table 2.

Comparative Example 4

Pure isopropanol was used as a starting material and fed to a reactor for dehydration, and the size of the tube of the isopropanol dehydration reactor was φ10×2.0.

The conditions for isopropanol dehydration included: a temperature of 300° C., a pressure of 0.3 MPa, a space velocity of the catalyst of 1.5 h$^{-1}$, and an isopropanol dehydration catalyst that was a heteropoly acid type catalyst. The product obtained was analyzed by gas chromatography.

Here, the water content of the isopropanol starting material was 3.0 wt %, and the isopropanol content of the product was 0.2 wt %.

The properties of the final propylene product, the conversion rate of isopropanol, the composition of alkene and alkyne impurities in the product and the energy consumption (energy consumption refers to the energy consumption per ton of product of the whole process when a qualified propylene product is produced by dehydration of isopropanol) are shown in Table 2.

TABLE 2

Conversion rate of isopropanol, product composition and energy consumption

| Name(s) | Conversion rate of isopropanol | Purity of propylene product, wt % | Ethylene content, ppm | Acetylene content, ppm | Methylacetylene and propadiene, ppm | Butene + butadiene, ppm | Comparison of energy consumption, % |
|---|---|---|---|---|---|---|---|
| Example 1 | 96.8% | 99.95 | 6 | 3 | 1 | 2 | 100 |
| Example 2 | 98.0% | 99.81 | 36 | 4 | 6 | 12 | 114.7 |
| Example 3 | 97.7% | 99.80 | 18 | 3 | 5 | 4 | 111.2 |
| Example 4 | 96.9% | 99.93 | 5 | 2 | 1 | 2 | 110.5 |
| Example 5 | 97.2% | 99.89 | 7 | 3 | 3 | 2 | 108.4 |
| Example 6 | 97.5% | 99.92 | 8 | 7 | 5 | 4 | 103.2 |
| Example 7 | 97.5% | 99.92 | 14 | 1 | 4 | 4 | 104.3 |
| Example 8 | 99.3% | 99.89 | 14 | 2 | 4 | 5 | 102.1 |
| Example 9 | 99.3% | 99.90 | 18 | 1 | 4 | 4 | 102.5 |
| Example 10 | 99.7% | 99.87 | 19 | 2 | 3 | 5 | 102.2 |
| Comparative Example 1 | 99.1% | 99.58 | 45 | 12 | 15 | 13 | 121.3 |
| Comparative Example 2 | 99.7% | 98.02 | 42 | 22 | 16 | 18 | 147.2 |
| Comparative Example 3 | 99.5% | 99.77 | 39 | 12 | 12 | 14 | 118.8 |
| Comparative Example 4 | 99.8% | 97.23 | 63 | 23 | 24 | 23 | 139.8 |

The invention claimed is:

1. A dehydration process, comprising a dehydration step of subjecting a starting material containing isopropanol to a dehydration reaction in the presence of a dehydration catalyst comprising alumina to produce a product containing propylene, wherein the starting material has a water content of 3.0 to 5.0 wt %, relative to 100 wt % of the total mass of the starting material, and the product has a total content of $C_2$ unsaturated impurities and $C_3$-$C_4$ unsaturated impurities of 80 ppm or less, relative to 100 wt % of the total mass of the product, wherein said product has a $C_2$ unsaturated impurities content of 50 ppm or less, and the conversion rate of isopropanol is 96.0-99.9%.

2. The dehydration process according to claim 1, wherein said product has a $C_2$ unsaturated impurities content of 30 ppm or less, relative to 100 wt % of the total mass of the product, and/or has a $C_3$-$C_4$ unsaturated impurities content of 30 ppm or less, relative to 100 wt % of the total mass of the product, and/or has a propylene content of 65.0 to 69.8 wt %, relative to 100 wt % of the total mass of the product.

3. The dehydration process according to claim 1, wherein said starting material has an isopropanol content of 90.0-99.9 wt %, relative to 100 wt % of the total mass of said starting material, and/or the conversion rate of isopropanol is 97.0-99.8%.

4. The dehydration process according to claim 1, wherein said dehydration catalyst comprising alumina is selected from solid acid catalysts comprising alumina.

5. The dehydration process according to claim 1, wherein the operating conditions of the dehydration step include: a reaction temperature of 150-450° C., a reaction pressure of 0.05-1.0 MPaG, and a volume space velocity of 0.05-5.0 h$^{-1}$.

6. The dehydration process according to claim 1, further comprising the step of separating an isopropanol/water mixture from said product,
or, further comprising the steps of:
1) washing the product with an absorbent to obtain a crude propylene product and a rich absorption liquid,
2) subjecting the crude propylene product to separation to remove heavy components, to obtain refined propylene, and
3) subjecting the rich absorption liquid to separation, to obtain an isopropanol/water mixture.

7. The dehydration process according to claim 6, wherein the mixture has a water content of 10-20 wt %, relative to 100 wt % of the total mass of the mixture.

8. The dehydration process according to claim 6, further comprising a recycling step of recycling 90 wt % or more, or substantially 100 wt % of the mixture to the dehydration step.

9. The dehydration process according to claim 8, wherein in the recycling step, the at least a portion of the mixture is mixed with the starting material of the dehydration step, optionally supplemented with an additional amount of water, to increase or decrease) the water content of the staring material to a predetermined level.

10. The dehydration process according to claim 1, further comprising the step of measuring the $C_3$-$C_4$ unsaturated impurities content of the product and comparing the measured value of the $C_3$-$C_4$ unsaturated impurities content (in ppm) with a preset value, wherein when the measured value of the $C_3$-$C_4$ unsaturated impurities content is greater than the preset value, the conversion rate of isopropanol is measured to obtain a measured value (set as C, in %) of said conversion rate, in which:
1) when the measured value C is between 96.0% and 99.0%, the water content of the starting material is increased by 0.01 to 30 times, with a proviso that the water content after the increase is in a range of 0.1 to 3.0 wt % relative to 100 wt % of the total mass of the starting material,
2) when the measured value C is between 99.0% and 99.5%, the water content of the starting material is increased by 0.01 to 2 times with a proviso that the water content after the increase is in a range of 3.0 to 5.0 wt % relative to 100 wt % of the total mass of the starting material, and
3) when the measured value C is between 99.5% and 99.9%, the water content of the starting material is increased by 0.01 to 2 times with a proviso that the water content after the increase is in a range of 5.0 to 10.0 wt % relative to 100 wt % of the total mass of the starting material.

11. The dehydration process according to claim 1, further comprising the step of measuring the $C_2$ unsaturated impurities content of said product and comparing the measured value of the $C_2$ unsaturated impurities content (in ppm) with a preset value, wherein when the measured value of the $C_2$ unsaturated impurities content is greater than the preset value, the conversion rate of isopropanol is measured, to obtain a measured value (set as D, in %) of said conversion rate, in which:
1) when the measured value D is between 96.0% and 99.0%, the water content of the starting material is increased by 0.01-50 times with a proviso that the water content after the increase is in a range of 0.1 to 5.0 wt % relative to 100 wt % of the total mass of the starting material, and
2) when the measured value D is between 99.0% and 99.9%, the water content of the starting material is increased by 0.01-3 times with a proviso that the water content after the increase is in a range of 5.0 to 10.0 wt % relative to 100 wt % of the total mass of the starting material.

12. A method for producing propylene, comprising the steps of:
subjecting acetone as a starting material to a hydrogenation reaction in the presence of a hydrogenation catalyst to produce a product containing isopropanol,
separating the isopropanol-containing product to obtain a hydrogen-containing gas and an isopropanol-containing liquid,
separating the isopropanol-containing liquid to obtain isopropanol,
dehydrating the isopropanol to produce a propylene-containing product according to the dehydration process of claim 1,
washing the propylene-containing product with an absorbent to obtain a crude propylene product and a rich absorption liquid,
separating the rich absorption liquid to obtain an isopropanol/water azeotrope,
separating and removing heavy components from the crude propylene product to obtain refined propylene.

13. The method according to claim 12, further comprising the step of:
recycling at least a portion of the isopropanol/water azeotrope to the dehydration step.

14. A plant for producing propylene by the dehydration process of claim 1, comprising an acetone hydrogenation reactor, a hydrogenation product gas-liquid separator, a fractionating tower, an isopropanol dehydration reactor, a propylene absorption-separation tower, an azeotropic distillation tower and a crude propylene de-heavy fractionator connected in sequence, wherein the acetone hydrogenation reactor is configured to perform hydrogenation reaction on acetone used as a starting material in the presence of a hydrogenation catalyst to produce an isopropanol-containing product, the hydrogenation product gas-liquid separator is configured to separate the isopropanol-containing product to obtain a hydrogen-containing gas and an isopropanol-containing liquid, the fractionating tower is configured to separate the isopropanol-containing liquid to obtain isopropanol, the isopropanol dehydration reactor is configured to perform dehydration reaction on the isopropanol used as a starting material in the presence of an alumina-containing dehydration catalyst to produce a propylene-containing product, the propylene absorption-separation tower is configured to wash the propylene-containing product with an absorbent to obtain a crude propylene product and a rich absorption liquid, the azeotropic distillation tower is configured to separate the rich absorption liquid to obtain an isopropanol/water azeotrope, the crude propylene de-heavy fractionator is configured to separate and remove heavy components from the crude propylene product to obtain refined propylene, and a material outlet at the top and/or upper part of the azeotropic distillation tower is in communication with a material inlet of the isopropanol dehydration reactor.

15. The plant according to claim 14, wherein at least two measurers, at least one comparator and at least one controller are provided at the product outlet of the isopropanol dehydration reactor, and in the at least two measurers, at least one is configured to measure the $C_3$-$C_4$ unsaturated impurities content and/or the $C_2$ unsaturated impurities content of the product to obtain a measured value of the content, and at least one is configured to measure the conversion rate of isopropanol to obtain a measured value of the conversion rate, the at least one comparator is configured to compare the measured values with the preset values, and to issue instructions to said at least one controller based on the comparison result and said measured value of the conversion rate, the at least one controller is configured to execute the instructions to increase the water content of the starting material of the isopropanol dehydration reactor.

16. The dehydration process according to claim 4, wherein said dehydration catalyst comprising alumina is amorphous silica-alumina having an alumina content of 1-30 wt %, with the balance being silica, and/or said amorphous silica-alumina having been subjected to a saturated steam treatment at 300-500° C.

17. The dehydration process according to claim 6, wherein said absorbent is at least one selected from the group consisting of water and isopropanol, and/or said crude propylene product is separated by rectification, and/or said rich absorption liquid is separated by rectification, and/or said isopropanol/water mixture is an azeotrope.

18. The dehydration process according to claim 7, wherein the mixture has a water content of 12-13 wt %, relative to 100 wt % of the total mass of the mixture.

19. The dehydration process according to claim 10, wherein:

in 1), when a planar rectangular coordinate system is established with the value of the conversion rate of isopropanol (in %) as an abscissa (with a starting point of 96.0 and an end point of 99.0), with the value of the water content of the starting material (in wt %) as an ordinate (with a starting point of 0.1 and an end point of 3.0) and with the coordinate (0, 0) as the origin point, a straight line segment is drawn from the coordinate (96.0, 0.1) to the coordinate (99.0, 3.0), and assuming that the coordinate of the measured value C on the straight line segment is set as (C, A1), where A1 represents the value of the water content corresponding to the measured value C on the straight line segment, then a value in a range of A1 to 3.0 is selected as the value of the water content after the increase, and/or in 2), when a planar rectangular coordinate system is established with the value of the conversion rate of isopropanol (in %) as an abscissa (with a starting point of 99.0 and an end point of 99.5), with the value of the water content of the starting material (in wt %) as an ordinate (with a starting point of 3.0 and an end point of 5.0) and with the coordinate (0, 0) as the origin point, a straight line segment is drawn from the coordinate (99.0, 3.0) to the coordinate (99.5, 5.0), and the coordinate of the measured value C on the straight line segment is set as (C, A2), wherein A2 represents the value of the water content corresponding to the measured value C on the straight line segment, a value in a range of A2 to 5.0 is selected as the value of the water content after the increase, and/or in 3), when a planar rectangular coordinate system is established with the value of the conversion rate of isopropanol (in %) as an abscissa (with a starting point of 99.5 and an end point of 99.9), with the value of the water content of the starting material (in wt %) as an ordinate (with a starting point of 5.0 and an end point of 10.0) and with the coordinate (0, 0) as the origin point, a straight line segment is drawn from the coordinate (99.5, 5.0) to coordinate (99.9, 10.0), and assuming that the coordinate of the measured value C on the straight line segment is set as (C, A3), wherein A3 represents the value of the water content corresponding to the measured value C on the straight line segment, then a value in a range of A3 to 10.0 is selected as the value of the water content after the increase.

20. The dehydration process according to claim 19, wherein:
in 1), a value in a range of A1 to A1+(3.0-A1)/2 is selected as the value of the water content after the increase, and/or in 2), a value in a range of A2 to A2+(5.0-A2)/2 is selected as the value of the water content after the increase, and/or in 3), a value in a range of A3 to A3+(9.0-A3)/2 is selected as the value of the water content after the increase.

21. The dehydration process according to claim 11, wherein:
in 1), when a planar rectangular coordinate system is established with the value of the conversion rate of isopropanol (in %) as an abscissa (with a starting point of 96.0, and an end point of 99.0), with the value of the water content of the starting material (in wt %) as an ordinate (with a starting point of 0.1, and an end point of 5.0), and with the coordinate (0, 0) as the origin point, a straight line segment is drawn from the coordinate (96.0, 0.1) to the coordinate (99.0, 5.0), and assuming that the coordinate of the measured value D on the straight line segment is set as (D, B1), wherein B1 represents the value of the water content corresponding to the measured value D on the straight line segment, then a value in a range of B1 to 5.0 is selected as the value of the water content after the increase, and/or in 2), the water content after the increase is in a range of 5.0 to 9.0 wt %, relative to 100 wt % of the total mass of the starting material, and/or when a planar rectangular coordinate system is established with the value of the conversion rate of isopropanol (in %) as an abscissa (with a starting point of 99.0 and an end point of 99.9), with the value of the water content of the starting material (in wt %) as an ordinate (with a starting point of 5.0 and an end point of 10.0) and with the coordinate (0, 0) as the origin point, a straight line segment is drawn from the coordinate (99.0, 5.0) to the coordinate (99.9, 10.0), and assuming that the coordinate of the measured value D on the straight line segment is set as (D, B2), wherein B2 represents the value of the water content corresponding to the measured value D on the straight line segment, a value in a range of B2 to 10.0 is selected as the value of the water content after the increase.

22. The dehydration process according to claim 21, wherein:
in 1), a value in a range of B1 to B1+(5.0-B1)/2 is selected as the value of the water content after the increase, and/or in 2), a value in a range of B2 to B2+(9.0-B2)/2 is selected as the value of the water content after the increase.

* * * * *